United States Patent [19]

Geiser et al.

[11] Patent Number: 5,034,470
[45] Date of Patent: Jul. 23, 1991

[54] PROCESS FOR THE PREPARATION OF EPOXIDIZED SYNTHETIC CIS-1,4-POLYISOPRENE

[75] Inventors: Joseph F. Geiser, Uniontown; Dane K. Parker, Massillon; Richard G. Bauer, Kent; Kenneth F. Castner, Uniontown, all of Ohio

[73] Assignee: The Goodyear Tire & Rubber Company, Akron, Ohio

[21] Appl. No.: 576,913

[22] Filed: Sep. 4, 1990

[51] Int. Cl.$^5$ .............................................. C08F 8/08
[52] U.S. Cl. ................................ 525/360; 525/332.8; 525/332.9; 525/333.1; 525/333.2; 525/387
[58] Field of Search ................... 525/387, 360

[56] References Cited

U.S. PATENT DOCUMENTS 4,157,346  6/1979  Lincs et al. ..................... 260/348.31

FOREIGN PATENT DOCUMENTS 0159619  10/1985  European Pat. Off. .

OTHER PUBLICATIONS 114446z 38-Elastomers vol. 76 (1972).
Jian et al., Journal of Polymer Science: Part C: Polymer Letters, vol. 28, 285-288 (1990).
Venturello et al., J. Org. Chem. 53, 1553-1557 (1988).
Tutorskii et al., vol. 16, pp. 186-200 (1974).
Greenspan F. P., Chemical Reactions of Polymers, vol. 19, pp. 152-172.
Gemmer et al., Journal of Polymer Science, Polymer Chemistry Edition, vol. 16, 2985-2990 (1978).
67428w Chemical Abstracts, vol. 78 (1970).
Sharpless et al., Aldrichimica Acta, vol. 12, No. 4, pp. 63-74 (1979).
Khcheyan et al., Khim. Prom-st. (Moscow), (10) (1975).
Naumova et al., Vestsi Akad. Navuk BSSR Ser. Khim. Navuk, (2) pp. 98-90 (1987).
Roux et al., Journal of Polymer Science, Part C, No. 16, pp. 4687, 4693 (1969).

Primary Examiner—Bernard Lipman
Attorney, Agent, or Firm—Bruce J. Hendricks

[57] ABSTRACT

The present invention relates to a process for the preparation of epoxidized synthetic cis-1,4-polyisoprene. The process involves reacting the synthetic cis-1,4-polyisoprene in a $C_5$-$C_7$ aliphatic hydrocarbon with tertiary butyl hydroperoxide in the presence of a molybdenum catalyst at a reaction temperature ranging from about 20° C. to about 100° C. The molybdenum catalyst is prepared by reacting together under a $N_2$ atmosphere molybdenum pentachloride with a carboxylic acid of the formula:

$$CH_3(CH_2)_nCOOH$$

wherein n is an integer ranging from 8 to 28. The molar ratio of molybdenum pentachloride to the carboxylic acid ranges from about 1:1 to 1:3.

10 Claims, No Drawings

PROCESS FOR THE PREPARATION OF EPOXIDIZED SYNTHETIC CIS-1,4-POLYISOPRENE

BACKGROUND OF THE INVENTION

The present invention relates to a process for the preparation of epoxidized synthetic cis-1,4-polyisoprene. More particularly, the present invention involves a process for the preparation of epoxidized synthetic cis-1,4-polyisoprene in an aliphatic $C_5$–$C_7$ solution using tertiary butyl hydroperoxide and a particular molybdenum catalyst.

Epoxidized natural rubber has recently been commercialized and its use in various rubber products been investigated. The natural rubber may be epoxidized as a latex by the use of aqueous hydrogen peroxide. Since the epoxidized natural rubber has very selective applications due to its properties, it would be desirable to have an epoxidized form of synthetic cis-1,4-polyisoprene for applications not met by epoxidized natural rubber. Unfortunately, synthetic cis-1,4-polyisoprene is commercially produced by the catalytic polymerization of isoprene in a $C_5$–$C_7$ aliphatic hydrocarbon solution. Since isolation of the polyisoprene and subsequent modification would be less practical, it would be desirable to epoxidize the polyisoprene in the $C_5$–$C_7$ aliphatic hydrocarbon.

It is well known that tertiary butyl hydroperoxide has been used in the metal-catalyzed oxygenation of olefins. For example, K. Barry Sharpless et al, Aldrichimica Act, Vol. 12, No. 4, pages 63–74, (1979) disclose the use of tertiary butyl hydroperoxide in the molybdenum-catalyzed epoxidation of isolated olefins. Unfortunately, many conventional molybdenum catalysts are not readily soluble in $C_5$–$C_7$ aliphatic hydrocarbons. Another problem is the undesirable degradation of the polyisoprene from the epoxidization reaction. Therefore, there exists a need for an efficient method to produce epoxidized synthetic cis-1,4-polyisoprene without the substantial degradation of the end product.

SUMMARY OF THE INVENTION

The present invention relates to a process involving reacting synthetic cis-1,4-polyisoprene in a $C_5$–$C_7$ aliphatic hydrocarbon with tertiary butyl hydroperoxide in the presence of a particular molybdenum catalyst. The present process substantially eliminates the need of conventional polymer stabilizers associated with other methods of epoxidization with greatly reduced processing times. The present process is characterized by low reaction temperatures without the need of corrosive acids and polymer product degradation.

DETAILED DESCRIPTION OF THE INVENTION

There is disclosed a process for the preparation of epoxidized synthetic cis-1,4-polyisoprene comprising reacting synthetic cis-1,4-polyisoprene in a $C_5$–$C_7$ aliphatic hydrocarbon with tertiary butyl hydroperoxide in the presence of a molybdenum catalyst at a reaction temperature ranging from about 20° C. to about 100° C. wherein said catalyst is prepared by reacting together under a $N_2$ atmosphere molybdenum pentachloride and a carboxylic acid of the formula:

$$CH_3(CH_2)_nCOOH$$

wherein n is an integer ranging from 8 to 28 and the mole ratio of said molybdenum pentachloride to said carboxylic acid ranges from about 1:1 to 1:3.

The epoxidized synthetic cis-1,4-polyisoprene which is prepared in accordance with the present invention is a modified form of synthetic cis-1,4-polyisoprene in which some of the unsaturation is replaced by epoxide groups. The level of epoxide modification may range from about 2 to about 50 mole percent. Preferably, the level of epoxide modification will range from about 3 to about 30 mole percent, with a range of from about 10 to about 25 being particularly preferred. Typically, the epoxidized synthetic cis-1,4-polyisoprene will have a Mooney viscosity of 25 to 110 with a range of from about 40 to about 85 being preferred. The glass transition temperature (Tg) of the epoxidized synthetic cis-1,4-polyisoprene may range from about −69° C. to about −10° C., with a range of from about −55° C. to about −40° C. being preferred.

In accordance with the present invention, synthetic cis-1,4-polyisoprene is epoxidized in a $C_5$–$C_7$ aliphatic hydrocarbon cement. Representative of the hydrocarbons include pentane, hexane, and heptane. Preferably, the aliphatic hydrocarbon is hexane. The polyisoprene is dissolved in the aliphatic hydrocarbon in an amount ranging from about 5% to about 18% by weight/vol., with a range of from about 7% to about 10% by weight/vol. being preferred. In accordance with the preferred embodiment, since polyisoprene is commonly polymerized in a $C_5$–$C_7$ aliphatic hydrocarbon, the epoxidization follows the polymerization without an intervening isolation of the polyisoprene.

The synthetic cis-1,4-polyisoprene is reacted with tertiary butyl hydroperoxide. It has been discovered that water is deleterious to the reaction and, therefore, it is preferred to have as little present as possible. Tertiary butyl peroxide ranging from about 70 to 100 percent purity is generally used. Preferably, the tertiary butyl hydroperoxide has a purity of approximately 90% or higher.

The amount of tertiary butyl hydroperoxide is determined by the amount of epoxidation desired. Generally the amount of tertiary butyl hydroperoxide ranges from about 2 mole percent to about 50 mole percent, with a range of from about 10 mole percent to about 25 mole percent being preferred.

The epoxidization of the synthetic cis-1,4-polyisoprene is carried out in the presence of a molybdenum catalyst. The molybdenum catalyst is prepared by reacting molybdenum pentachloride with a carboxylic acid of the formula:

$$CH_3(CH_2)_nCOOH$$

wherein n is an integer ranging from about 8 to 28. The mole ratio of molybdenum pentachloride to carboxylic acid may range from about 1:1 to 1:3. Preferably, the mole ratio may range from about 1:1.25 to 1:2. In a particularly preferred mode, the mole ratio is approximately 1:1.5. Representative of the carboxylic acids for use in preparation of the molybdenum containing catalyst include capric acid, lauric acid, myristic acid, palmitic acid, stearic acid, and tricontanoic acid. The preferred carboxylic acids of the above structural formula are when n is an integer ranging from about 10 to 16.

The molybdenum containing catalysts are prepared by reacting molybdenum pentachloride with the carboxylic acid in the absence of a solvent. The reaction is conducted under a $N_2$ atmosphere at a temperature which may range from about 0° C. to 100° C. Preferably, the reaction temperature ranges from about 50° to 75° C. The reaction mixture is preferably agitated to ensure complete and uniform reaction of the materials. Generally speaking, the molybdenum pentachloride is first introduced to the reactor and the carboxylic acid is then added. After the reaction is complete, the reaction mixture is cooled to room temperature and may be diluted to the desired concentration with a $C_5$–$C_7$ hydrocarbon, preferably hexane.

The molybdenum containing catalysts for use in the process of the present invention are relatively soluble in the $C_5$–$C_7$ aliphatic hydrocarbon. In general, the catalyst is used in catalytic amounts which, of course, will vary depending upon the specific catalysts used, reactor design and relative amounts of the catalyst. For example, the amount of molybdenum catalyst may range from about 0.01 to about 0.25 mole percent of the unsaturation in the polyisoprene. Preferably, the amount of molybdenum catalyst ranges from about 0.05 to about 0.1.

One advantage of the present invention is that the polyisoprene is generally prepared in a $C_5$–$C_7$ aliphatic hydrocarbon and, therefore, does not have to be isolated prior to the epoxidization step. The epoxation reaction may be conducted in a batch operation or it may be in a continuous process. The epoxidization reaction may be carried out at a temperature ranging from about 20° C. to about 100° C. Preferably, the reaction is conducted at a temperature ranging from about 55° C. to about 70° C. Any suitable pressure may be used for the epoxidization reaction. Generally speaking, the pressure will range from about 1 atmosphere to about 3 atmosphere, with a range of from about 1 atmosphere to about 1.5 atmosphere being preferred.

The presence of high levels (approximately 2%) of chemicals (known as short stop) used to terminate the polymerization of isoprene may tend to destroy the activity of the molybdenum containing catalyst. One example of such chemical is triisopropanol amine. Preferably, these type of chemicals are removed from the reaction mixture prior to addition of the catalyst.

One of the advantages of the present invention is the efficient reaction time of the epoxidization reaction. For example, the epoxidization reaction may range from a period as short as 0.1 to a period of 6.0 hours. Preferably, the reaction is as rapid as possible and generally ranges from about 0.25 to about 2.0 hours.

EXAMPLE 1

Preparation of Molybdenum-2-Ethyl Hexanoate

Into a suitable reactor equipped with a $N_2$ purge, thermometer and mechanical stirrer was charged 1.51 grams (5.53 mM) of dry molybdenum pentachloride to a $N_2$ atmosphere. 1.19 grams (8.25 mM) of 2-ethylhexanoic acid were charged to the reactor and the reaction mixture heated to 65° C. with agitation. After 2 hours, the reaction mixture was cooled while maintaining a $N_2$ atmosphere. Hexane was added to the product to give a final volume of 70 ml and a final molybdenum concentration of 0.079 moles per liter (molarity).

EXAMPLE 2

Preparation of Molybdenum Octoate

Into a suitable reactor equipped with a $N_2$ purge, thermometer and mechanical stirrer was charged 1.28 grams (4.69 mM) of dry molybdenum pentachloride to a $N_2$ atmosphere. 1.02 grams (7.07 mM) of octanoic acid were charged to the reactor and the reaction mixture heated to 65° C. with agitation. After 2 hours, the reaction mixture was cooled while maintaining a $N_2$ atmosphere. Hexane was added to the product to give a final volume of 90.4 ml and a final molybdenum concentration of 0.052 moles per liter (molarity).

EXAMPLE 3

Preparation of Molybdenum Laurate

Into a suitable reactor equipped with a $N_2$ purge, thermometer and mechanical stirrer was charged 1.00 grams (3.66 mM) of dry molybdenum pentachloride to a $N_2$ atmosphere. 1.11 grams (5.54 mM) of lauric acid were charged to the reactor and the reaction mixture heated to 65° C. with agitation. After 2 hours, the reaction mixture was cooled while maintaining a $N_2$ atmosphere. Hexane was added to the product to give a final volume of 64 ml and a final molybdenum concentration of 0.057 moles per liter (molarity).

EXAMPLE 4

Preparation of Molybdenum Palmitate

Into a suitable reactor equipped with a $N_2$ purge, thermometer and mechanical stirrer was charged 1.45 grams (5.31 mM) of dry molybdenum pentachloride to a $N_2$ atmosphere. 2.04 grams (7.96 mM) of palmitic acid were charged to the reactor and the reaction mixture heated to 65° C. with agitation. After 2 hours, the reaction mixture was cooled while maintaining a $N_2$ atmosphere. Hexane was added to the product to give a final volume of 66 ml and a final molybdenum concentration of 0.080 moles per liter (molarity).

EXAMPLE 5

Preparation of Molybdenum Tricontanoate

Into a suitable reactor equipped with a $N_2$ purge, thermometer and mechanical stirrer was charged 1.67 grams (6.11 mM) of dry molybdenum pentachloride to a $N_2$ atmosphere. 4.14 grams (9.16 mM) of tricontanoic acid were charged to the reactor and the reaction mixture heated to 65° C. with agitation. After 2 hours, the reaction mixture was cooled while maintaining a $N_2$ atmosphere. Hexane was added to the product to give a final volume of 111 ml and a final molybdenum concentration of 0.055 moles per liter (molarity).

EXAMPLE 6

Preparation of Molybdenum Benzoate

Into a suitable reactor equipped with a $N_2$ purge, thermometer and mechanical stirrer was charged 1.79 grams (6.55 mM) of dry molybdenum pentachloride to a $N_2$ charged to the reactor and the reaction mixture heated to 65° C. with agitation. After 2 hours, the reaction mixture was cooled while maintaining a $N_2$ atmosphere. Hexane was added to the product to give a final volume of 66 ml and a final molybdenum concentration of 0.099 moles per liter (molarity).

EXAMPLE 7

Preparation of Molybdenum Stearate

Into a suitable reactor equipped with a $N_2$ purge, thermometer and mechanical stirrer was charged 236 grams (864 mM) of dry molybdenum pentachloride to a $N_2$ atmosphere. 350.4 grams (1300 mM) of stearic acid were charged to the reactor and the reaction mixture heated to 65° C. with agitation. After 2 hours, the reaction mixture was cooled while maintaining a $N_2$ atmosphere. Hexane was added to the product to give a final volume of 1148 ml and a final molybdenum concentration of 0.75 moles per liter (molarity).

EXAMPLE 8

Epoxidation of Synthetic Cis-1,4-Polyisoprene

The reactor consisted of a 1 liter 4 neck Pyrex resin kettle equipped with a mechanical Teflon ® stir blade, thermometer, and reflex condenser. An ethylene glycol bath controlled by a Thermowatch regulator was used to heat the reactor.

To the reactor was added 475 ml of hexane and 23.8 grams (0.35 moles of unsaturation) of synthetic cis-1,4-polyisoprene. The solution was heated and stirred under a nitrogen blanket until dissolved to give 7.6% wt/vol cement. To this was added the molybdenum containing catalyst and the solution was stirred 0.5 hours at 60° C. 0.035 mole of the tertiary butyl hydroperoxide was then added to the solution. The 70% aqueous grade, 90% aqueous and anhydrous (3.0 M) was purchased from Aldrich Chemical Company. The 70% dried grade was freshly prepared by extracting the 70% aqueous grade into hexane and drying over anhydrous sodium sulfate.

The reaction was monitored by withdrawing 3-5 ml aliquots for NMR analysis. The aliquots were then coagulated with isopropyl alcohol, followed by mastication in acetone and pressing into a thin film to be first vacuum dried then air dried. A portion of the dry sample was then redissolved in deuterated chloroform containing 1% tetramethyl silane and analyzed by NMR.

After the completion of the reaction (final), the reaction mixture was worked-up by coagulation with alcohol (mixture of isopropanol and methanol), soaked for 1 hour in acetone and the polymer dried, first under vacuum, then overnight in an open air oven hood at 25° C.

For the purpose of comparison, samples 1-21 are controls. Samples 22-32 represent the present invention. Samples 1-6 used molybdenum hexacarbonyl, $Mo(Co)_6$, to catalyze the reaction. The molybdenum hexacarbonyl was commercially purchased from Alpha Research Chemicals and Materials. Samples 7-17 used molybdenum acetylacetonate (MoAcAc). The molybdenum acetylacetone used in Samples 7-13 and 17 was supplied by Climax Chemicals. The molybdenum acetylacetone used in Samples 14-61 was supplied by Aldrich. Sample 18 used a branched molybdenum octoate which was commercially purchased from Mooney Chemicals under the tradename Molybdenum Hex-Chem TM (MoHexChem TM). Sample 19 used molybdenum benzoate (MolyBenz) prepared in Example 6. Sample 20 used molybdenum octoate (MolyOct) prepared in Example 2. Sample 21 used molybdenum 2-ethylhexanoate (MolyEtHex) prepared in Example 1. Sample 22 used molybdenum laurate (MolyLaur) prepared in Example 3. Sample 23 used molybdenum palmitate (MolyPalm) prepared in Example 4. Samples 24-37 used molybdenum stearate (MolySt) prepared in Example 8. Sample 38 used molybdenum tricontanoate (MolyTricon) prepared in Example 5.

TABLE I

| Sample | Catalyst | Mole % of Catalyst | TBHP | Temperature °C. | Solvent | Mole % Epoxy 0.5 Hr. | Final Mole % Epoxy | Total Reaction Time (Hours) | Mooney Viscosity |
|---|---|---|---|---|---|---|---|---|---|
| 1 | $Mo(CO)_6$ | 0.1 | 70% aq. | 100 | Toluene | — | 13 | 2 | |
| 2 | $Mo(CO)_6$ | 0.1 | 70% aq. | 100 | Toluene | — | 10 | 2 | |
| 3 | $Mo(CO)_6$ | 0.5 | 70% aq. | 68 | Hexane | — | 0 | 2 | |
| 4 | $Mo(CO)_6$ | 0.5 | 70% aq. | 100 | Toluene | — | 10 | 2 | |
| 5 | $Mo(CO)_6$ | 0.5 | 70% aq. | 80 | Toluene | 0 | 0 | 1 | |
| 6 | $Mo(CO)_6$ | 0.5 | 70% aq. | 100 | Toluene | 13 | — | — | |
| 7 | MoAcAc | 0.5 | 70% aq. | 80 | Toluene | — | 10 | 1 | |
| 8 | MoAcAc | 0.5 | 70% aq. | 65 | Hexane | — | 10 | 1 | |
| 9 | MoAcAc | 0.5 | 70% aq. | 68 | Hexane | — | 5 | 2 | |
| 10 | MoAcAc | 0.25 | 70% aq. | 65 | Hexane | — | 7 | 4 | |
| 11 | MoAcAc | 0.25 | 70% aq. | 62 | Hexane | — | 20 | 1 | |
| 12 | MoAcAc | 0.125 | 70% aq. | 62 | Hexane | — | 3 | 24 | |
| 13 | MoAcAc | 0.125 | 70% dried | 62 | Hexane | — | 6 | 3 | |
| 14 | MoAcAc | 0.125 | 70% dried | 62 | Hexane | — | 3.3 | 24 | |
| 15 | MoAcAc | 0.125 | 70% dried | 62 | Hexane | — | 5 | 24 | |
| 16 | MoAcAc | 0.125 | 70% dried | 62 | Hexane | — | 3 | 72 | |
| 17 | MoAcAc | 0.125 | 70% dried | 62 | Hexane | — | 12 | 1 | |
| 18 | MoHexChem TM | .05 | 90% aq. | 65 | Hexane | 0 | 0 | 2 | |
| 19 | MolyBenz | .05 | 90% aq. | 62 | Hexane | 0 | 0 | 5 | 89 |
| 20 | MolyOct | .05 | 90% aq. | 62 | Hexane | 3.0 | 4.6 | 5 | Degraded |
| 21 | MolyEtHex | .05 | 90% aq. | 62 | Hexane | 3.7 | 10.0 | 6 | 58 |
| 22 | MolyLaur | .05 | 90% aq. | 62 | Hexane | 11.1 | 11.3 | 3 | 96 |
| 23 | MolyPalm | .05 | 90% aq. | 62 | Hexane | 12.0 | 9.7 | 4 | 104 |
| 24 | MolySt | .05 | 70% dried | 60 | Hexane | — | 10 | 1 | |
| 25 | MolySt | .05 | 70% dried | 60 | Hexane | — | 1 | 2 | |
| 26 | MolySt | .05 | 70% dried | 62 | Hexane | — | 10 | 1 | |
| 27 | MolySt | .05 | 70% dried | 62 | Hexane | — | 4 | 4.5 | |
| 28 | MolySt | .05 | 70% dried | 62 | Hexane | — | 5 | 3.5 | |
| 29 | MolySt | .05 | 70% dried | 62 | Hexane | — | 5 | 4 | |
| 30 | MolySt | .05 | 70% aq. | 62 | Hexane | — | 0 | 24 | |
| 31 | MolySt | .05 | 3 molar | 62 | Hexane | 12 | — | — | |
| 32 | MolySt | .05 | 90% aq. | 82 | Hexane | 6.5 | 2 | | 56 |
| 33 | MolySt | .05 | 90% aq. | 62 | Hexane | 8.4 | 2 | | 46 |
| 34 | MolySt | .05 | 90% aq. | 82 | Hexane | 10.7 | 2 | | 51 |
| 35 | MolySt | .05 | 90% aq. | 71 | Hexane | 6.8 | 2 | | 63 |
| 36 | MolySt | .05 | 90% aq. | 60 | Hexane | 7.9 | 2 | | 44 |
| 37 | MolySt | .05 | 90% aq. | 60 | Hexane | 7.0 | 2 | | 53 |

TABLE I-continued

| Sample | Catalyst | Mole % of Catalyst | TBHP | Temperature °C. | Solvent | Mole % Epoxy 0.5 Hr. | Final Mole % Epoxy | Total Reaction Time (Hours) | Mooney Viscosity |
|---|---|---|---|---|---|---|---|---|---|
| 38 | MolyTricon | .05 | 90% aq. | 62 | Hexane | 9.4 | 10 | 4 | 58.5 |

What is claimed is:

1. A process for the preparation of epoxidized synthetic polyisoprene comprising reacting synthetic cis-1,4-polyisoprene in a $C_5$–$C_7$ aliphatic hydrocarbon with tertiary butyl hydroperoxide in the presence of a molybdenum containing catalyst at a reaction temperature ranging from about 20° C. to about 100° C. wherein said catalyst is prepared by reacting under a $N_2$ atmosphere molybdenum pentachloride with a carboxylic acid of the formula:

$CH_3(CH_2)_n COOH$ wherein n is an integer ranging from about 8 to about 28 and the molar ratio of said molybdenum pentachloride to said carboxylic acid ranges from about 1:1 to 1:3.

2. The process of claim 1 wherein n is 10 to 16.

3. The process of claim 1 wherein said $C_5$-$C_7$ aliphatic hydrocarbon is hexane.

4. The process of claim 1 wherein the tertiary butyl hydroperoxide ranges from about 70% to 100 purity.

5. The process of claim 4 wherein the tertiary butyl hydroperoxide has a purity of 90%.

6. The process of claim 1 wherein said molar ratio of molybdenum pentachloride to carboxylic acid ranges from about 1:1.25 to 1:2.

7. The process of claim 1 wherein the amount of molybdenum containing catalyst ranges from about 0.01 to about 0.25 mole percent of the unsaturation in the polyisoprene.

8. The process of claim 1 wherein the reaction temperature ranges from about 55° C. to about 70° C.

9. The process of claim 1 wherein said polyisoprene is dissolved in said $C_5$-$C_7$ aliphatic hydrocarbon in an amount ranging from about 5% by weight to about 18% by weight/vol.

10. The process of claim 9 wherein said polyisoprene is dissolved in said $C_5$-$C_7$ aliphatic hydrocarbon in an amount ranging from about 7% by weight to about 10% by weight/vol.

* * * * *

UNITED STATES PATENT AND TRADEMARK OFFICE
CERTIFICATE OF CORRECTION

PATENT NO. : 5,034,470
DATED : July 23, 1991
INVENTOR(S) : Joseph Frank Geiser, Dane Kenton Parker, Richard George Bauer and Kenneth Floyd Castner It is certified that error appears in the above-identified patent and that said Letters Patent is hereby corrected as shown below:

At Column 6, line 15, delete "acetylacetone" and insert therefor --acetyl acetonate--.

At Column 6, lines 16-17, delete "acetylacetone" and insert therefor --acetyl acetonate--.

Signed and Sealed this

Twentieth Day of April, 1993

*Attest:*

MICHAEL K. KIRK

*Attesting Officer*   *Acting Commissioner of Patents and Trademarks*